Nov. 13, 1934. J. B. THOMPSON Plant Pat. 111
PLUM
Filed June 20, 1934
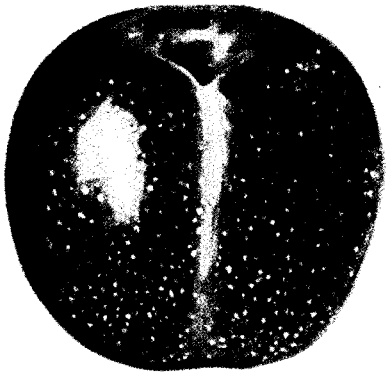
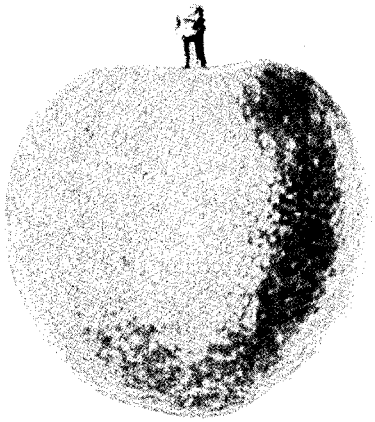
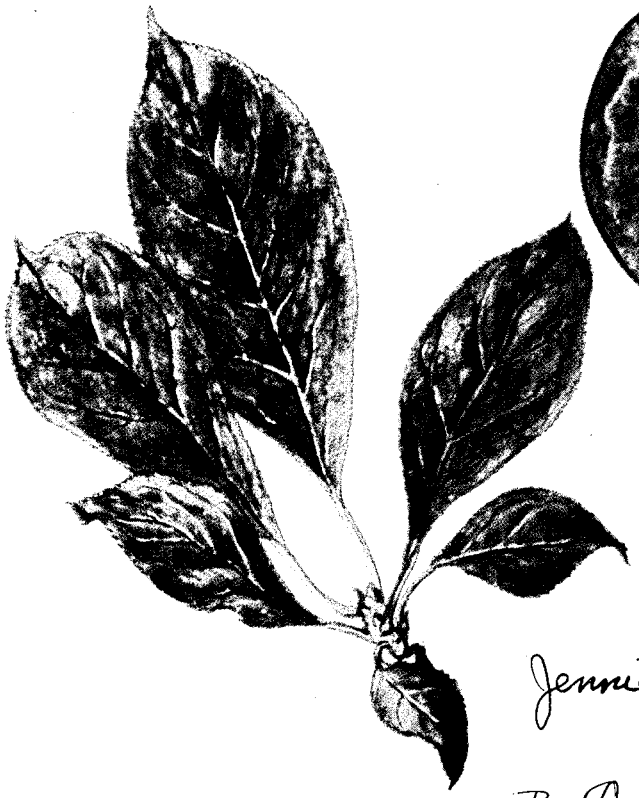
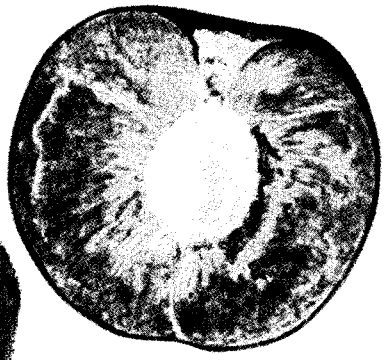
INVENTOR
Jennie Benedict Thompson
By Orville M. Kile
PLANT PATENT AGENT Patented Nov. 13, 1934

Plant Pat. 111

UNITED STATES PATENT OFFICE

111

PLUM

Jennie Benedict Thompson, Pasadena, Calif., assignor to Armstrong Nurseries, Inc., Ontario, Calif.

Application June 20, 1934, Serial No. 731,535

1 Claim. (Cl. 47—62)

My invention relates to a new and distinct variety of plum, developed from an unnamed seedling in Colorado, seed being procured from this seedling in 1919. The fruit of the new variety was first observed in 1923 but was not asexually reproduced until it was budded both on young stock and top-worked mature trees in Ontario, California, in 1932.

This new plum of deep maroon color has extraordinary characteristics of flavor, shape, flesh and skin colors, shipping qualities, and other features which make it a valuable commercial fruit differing materially from all other known varieties.

The accompanying illustration and specification disclose this new variety in detail.

*Tree.*—A vigorous grower, attaining medium to large size. The twigs are brownish with patches of gray.

*Foliage.*—The mature leaves of normal growth are 3¼ to 3½ inches long with a petiole ¾ to ⅞ inch long and at the point of greatest width approximately 1½ inches wide, pointed at end and edged completely by extremely fine serrations, each individual serration ending in a very short but spine-like growth. The texture is medium to fine rather than heavy or coarse.

The upper surfaces of the leaves are glossy rather than dull, also smooth, and moderately veined. The leaves occur in groups of three to five, each group including a variety of sizes. The color is approximately "forest green" (Plate XVII, Ridgway's Color Standards and Nomenclature).

*Fruit*

*Form.*—The form is round, almost perfectly globular with the exception of cavity and shallow suture. Apex very obtusely pointed. Large in size, measuring ordinarily 2 to 2¼ inches at the axial diameter and about the same at the greatest transverse diameter. The stem is short and thick and the cavity deep and narrow, thus causing the fruit to hang close to the branch. The suture, though shallow, is distinct and reaches from stem to apex.

*Color.*—When the heavy bloom is removed from the surface, the fruit is deep maroon to reddish maroon. The surface is thickly speckled with small light-colored specks, except at and near the cavity. In nature the fruit is covered with a heavy purplish or mauve bloom. This bloom does not entirely obscure the color beneath but only a slight suggestion of the rich maroon shows through.

A cross section of the ripe fruit shows the flesh a deep red color with a few light lines mostly radiating from the seed cavity. The color is rather uniform throughout but slightly darker near the skin than toward the seed. More technically speaking, the color of the flesh is predominantly "Bordeaux red" (Plate XII Ridgway's Color Standards and Nomenclature), with touches of "Carmine" (Plate I, Ridgway's).

*Skin.*—Thick, sufficiently tough to afford excellent protection for shipping, and adheres to the flesh closely.

*Stone.*—Comparatively small, measuring about one inch in its longest dimension, regular in form, flat, and while readily removed from the ripe fruit, some of the flesh clings to it. Yellowish in color.

*Flesh.*—Firm, becoming quite juicy in the fully ripened fruit.

*Flavor.*—Quite sweet and very pleasing even when the fruit is still firm and not fully mature. Most plums are rather tart and sour until they have fully ripened. The skin of this variety is less bitter than the skins of the two most nearly comparable varieties—Satsuma and Duarte. In this new variety even the skin is sweet in taste.

This plum is a freestone, whereas the Satsuma is a semi-cling. This plum differs from the Duarte in shape; it is round, whereas the Duarte is obovate or egg-shaped. It ripens ten days to two weeks before the Duarte.

Having thus disclosed this new plum which, it must be understood, may vary slightly in characteristics in different climates and soils;

What is claimed is:

The variety of plum tree herein described characterized particularly by its globular, sweet-flavored, maroon-colored fruits having rather thick, sweet skins.

JENNIE BENEDICT THOMPSON.